(12) United States Patent
Shi et al.

(10) Patent No.: US 10,660,766 B2
(45) Date of Patent: May 26, 2020

(54) BONE TRABECULAR FUSION CAGE

(71) Applicant: Beijing Chunlizhengda Medical Instruments Co., Ltd., Beijing (CN)

(72) Inventors: Chunbao Shi, Beijing (CN); Peng Xiao, Beijing (CN); Fengbao Xie, Beijing (CN); Chunlin Shen, Beijing (CN); Xiangxiang Xu, Beijing (CN); Dezhi Li, Beijing (CN)

(73) Assignee: Beijing Chunlizhengda Medical Instruments Co., Ltd., Beijing (CN)

(*) Notice: Subject to any disclaimer, the term of this patent is extended or adjusted under 35 U.S.C. 154(b) by 0 days.

(21) Appl. No.: 16/182,346

(22) Filed: Nov. 6, 2018

(65) Prior Publication Data
US 2019/0070017 A1 Mar. 7, 2019

Related U.S. Application Data

(63) Continuation of application No. PCT/CN2016/097825, filed on Sep. 1, 2016.

(30) Foreign Application Priority Data

May 6, 2016 (CN) .......................... 2016 1 0297282

(51) Int. Cl.
*A61F 2/44* (2006.01)
*A61F 2/30* (2006.01)
(Continued)

(52) U.S. Cl.
CPC ........ *A61F 2/4455* (2013.01); *A61F 2/30771* (2013.01); *A61F 2/44* (2013.01);
(Continued)

(58) Field of Classification Search
CPC ..................................... A61F 2/44–2002/4495
See application file for complete search history.

(56) References Cited

U.S. PATENT DOCUMENTS 6,436,142 B1* 8/2002 Paes ................... A61B 17/8615
623/17.15
8,562,685 B2* 10/2013 Ullrich, Jr. .............. A61F 2/442
623/17.11
(Continued)

FOREIGN PATENT DOCUMENTS

CN 101224143 A 7/2008
CN 101272750 A 9/2008
(Continued)

*Primary Examiner* — Zade Coley
(74) *Attorney, Agent, or Firm* — Wayne & Ken, LLC; Tony Hom

(57) ABSTRACT

A bone trabecular fusion cage for implanting into an intervertebral disc is disclosed. The fusion cage includes a bone trabecular housing made of titanium alloy powder material with trabecular housing accommodation space therein. A side wall of the bone trabecular housing is provided with a plurality of pores, and sclerotin can grow into the bone trabecular housing through the pores to securely fix the bone trabecular fusion cage in the intervertebral disc; and a liner made of polyether-ether-ketone material and fixed in the accommodating space of the bone trabecular housing, wherein the polyether-ether-ketone liner gpores can provide good elastic modulus of bone. With the product of the present disclosure, bone implantation is not required, the patient recovers fast, and excellent fusion effect can be obtained.

5 Claims, 6 Drawing Sheets

(51) Int. Cl.
*A61L 27/18* (2006.01)
*A61F 2/46* (2006.01)

(52) U.S. Cl.
CPC .............. *A61F 2/442* (2013.01); *A61F 2/447* (2013.01); *A61L 27/18* (2013.01); *A61F 2/4611* (2013.01); *A61F 2002/3082* (2013.01); *A61F 2002/3092* (2013.01); *A61F 2002/3093* (2013.01); *A61F 2002/30774* (2013.01); *A61F 2002/30784* (2013.01); *A61F 2002/30904* (2013.01); *A61F 2002/4629* (2013.01); *A61F 2310/00023* (2013.01); *A61L 2430/38* (2013.01)

(56) References Cited

U.S. PATENT DOCUMENTS

| | | | |
|---|---|---|---|
| 9,186,257 B2 * | 11/2015 | Geisler | A61F 2/447 |
| 2002/0165550 A1 * | 11/2002 | Frey | A61B 17/025 |
| | | | 606/85 |
| 2003/0187506 A1 * | 10/2003 | Ross | A61F 2/442 |
| | | | 623/17.13 |
| 2007/0027544 A1 * | 2/2007 | McCord | A61F 2/447 |
| | | | 623/17.11 |
| 2008/0161927 A1 * | 7/2008 | Savage | A61F 2/4455 |
| | | | 623/17.16 |
| 2008/0183292 A1 | 7/2008 | Trieu | |
| 2010/0262244 A1 | 10/2010 | Savage-Erickson et al. | |
| 2011/0071635 A1 | 3/2011 | Zhang et al. | |
| 2012/0265306 A1 * | 10/2012 | Trieu | A61F 2/442 |
| | | | 623/17.16 |
| 2014/0277482 A1 | 9/2014 | Gfeller et al. | |
| 2014/0277508 A1 | 9/2014 | Baynham | |
| 2015/0018956 A1 * | 1/2015 | Steinmann | A61F 2/447 |
| | | | 623/17.16 |
| 2015/0305878 A1 * | 10/2015 | O'Neil | A61B 5/45 |
| | | | 623/17.16 |
| 2016/0270931 A1 * | 9/2016 | Trieu | A61F 2/30942 |

FOREIGN PATENT DOCUMENTS

| | | |
|---|---|---|
| CN | 103445883 A | 12/2013 |
| CN | 203555820 U | 4/2014 |
| CN | 104010595 A | 8/2014 |

* cited by examiner

BONE TRABECULAR FUSION CAGE

CROSS-REFERENCE TO RELATED APPLICATIONS

This application is a continuation of International Application No. PCT/CN2016/097825 with a filing date of Sep. 1, 2016, designating the United States, and further claims to Chinese Application No. 201610297282.5 with a filing date of May 6, 2016. The content of the aforementioned applications, including any intervening amendments thereto, are incorporated herein by reference.

TECHNICAL FIELD

The present disclosure relates to a medical device, and more particularly to a bone trabecular fusion cage for implanting into an intervertebral disc.

BACKGROUND

The principle of treatment for lumbar instability is that, if symptoms are not relieved after conservative treatment for symptoms with obvious neurological stress, it is an indication for surgical treatment. Initially, surgical treatment adopts intervertebral disc nucleus pulposus removal with spinal canal decompression, in which the nucleus pulposus and annulus fibrosis were removed by posterior incision of the intervertebral disc, thereby enlarging the spinal canal decompression and relieving the compression of the spinal cord and nerve roots. However, since the removal of the lamina destroys the structure of the spine, a new instability factor is created in the spine, and the compression of the intervertebral space is not restored, resulting in a higher recurrence rate after surgery.

Later, intervertebral disc removal with spinal fusion surgery is used, in which various methods of interbody fusion are performed on the basis of spinal canal decompression and nucleus pulposus removal, such as interspinous bone graft fusion, intertransverse bone graft fusion, bone graft together with internal fixation device fusion and so on. The purpose of this type of fusion surgery is to increase the strength of the intervertebral structure and eliminate the instability of the spine caused by laminectomy. However, the height of the intervertebral space is not restored, and the intervertebral activity disappears after fusion, resulting in accelerated degeneration of adjacent intervertebral discs. From a wide range of perspectives, the reduction of activity of a single intervertebral activity is also an "unstable" condition. Therefore, there are still many patients with postoperative bone graft loosening, fracture, absorption, and loosening and fracture of internal fixation devices.

The traditional fusion cage material is pure polyether-ether-ketone (PEEK) material or pure bone trabecular material. The singleness of the material makes the performance of the product greatly compromised. Good elastic modulus of human bone is obtained but no bone growth effect is achieved. The two cannot coexist. Therefore, the patient's postoperative recovery is slow, and the fusion effect is relatively poor. In addition, as shown in FIG. 1 and FIG. 2, the current traditional fusion cage surgery requires the implantation of two fusion cages. The operation is complicated and difficult, which leads to large and plural wounds, more bleeding, slow postoperative recovery, and relatively poor fusion effect.

SUMMARY

It is an object of the present disclosure to provide a bone trabecular fusion cage that is capable of better bone ingrowth.

To achieve the above object, specific technical solutions of a bone trabecular fusion cage of the present disclosure are as follows.

A bone trabecular housing made of titanium alloy powder material and comprising trabecular housing accommodation space therein, wherein a side wall of the bone trabecular housing is provided with a plurality of pores, and sclerotin can grow into the bone trabecular housing through the pores to securely fix the bone trabecular fusion cage in the intervertebral disc; and a liner made of polyether-ether-ketone material and fixed in the accommodating space of the bone trabecular housing, wherein the polyether-ether-ketone liner gpores can provide good elastic modulus of bone. With the product of the present disclosure, bone implantation is not required, the patient recovers fast, and excellent fusion effect can be obtained.

Further, an inner wall of the bone trabecular housing is provided with a protrusion, an outer wall of the liner is provided with a recess that matches with the protrusion, and the protrusion of the bone trabecular housing is embedded in the recess of the liner to securely connect the bone trabecular housing and the liner.

Further, the protrusion in the bone trabecular housing is of beam-shape, and the recess of the liner has an interference fit with the beam-shaped protrusion of the bone trabecular housing.

Further, an implantation hole and an implantation groove are disposed at one end of the bone trabecular housing, the implantation groove is disposed on an end face of the bone trabecular housing, and the implantation hole is located in the implantation groove. Through connection of an implantation surgical tool matching with the implantation hole and the implantation groove to the bone trabecular housing, the bone trabecular fusion cage is inserted into the intervertebral disc through the intervertebral space for fixation.

Further, the bone trabecular housing has a convex end at one end and a flat end at the other end, and the implantation hole and the implantation groove are disposed on the flat end.

Further, the implant hole is a threaded hole.

Further, an appearance of the bone trabecular housing is a smooth transitional curvature, which gradually contracts from middle to opposite ends.

Further, the curvature of an outer contour of the bone trabecular housing is designed in accordance with a cross-sectional curvature of a spinal vertebral body of a patient.

Further, the plurality of pores on the side wall surface of the bone trabecular housing form a hollow mesh structure.

Further, the pores do not pentrate the side wall.

The advantages of the bone trabecular fusion cage of the present disclosure are:

1) The improved product does not require postoperative development after development of the needle, and the polyether-ether-ketone liner can provide good elastic modulus of bone. The bone trabecular housing can achieve better bone ingrowth. The product does not require bone grafting, and overcomes the problem that the singleness of the material makes the performance of the product greatly compromised. Also, better elastic modulus of bone and bone ingrowth effect are taken into consideration, the patient recovers quickly, and the fusion effect is good;

2) By using the bone trabecular fusion cage, products implanted into patient bodies are safer and more effective;

3) The shape and structure of the product are more in line with the human anatomy, which enables the doctor to easily implant the implant into the human body. Within a few months after implantation, the capillaries and related tissues will grow into the product along the pores of the housing, so that the implant is integrated with the human body and thus no loosening or displacement would occur;

4) The product can be conveniently and easily implanted. Designed implantation instrument is used which is threadedly connected with the tail of the fusion cage, passes through the intervertebral space, and is implanted into the intervertebral disc pretreated with other instruments. The bone ingrowth after implantation is huge, which can stabilize the intervertebral disc, so that better bone fusion is achieved. Compared with other fusion cages that require bone grafting, the results will be much better;

5) From the doctor's point of view, the product can be operated conveniently and quickly during surgery. The surgery is accessed from one position, the wound is treated well, and good imaging effect of metal position is achieved, which greatly reduces the difficulty of surgery.

DETAILED DESCRIPTION OF EMBODIMENTS

In order to better understand the object, structure and function of the present disclosure, a bone trabecular fusion cage of the present disclosure will be further described in detail below with reference to the accompanying drawings.

Figure 1:
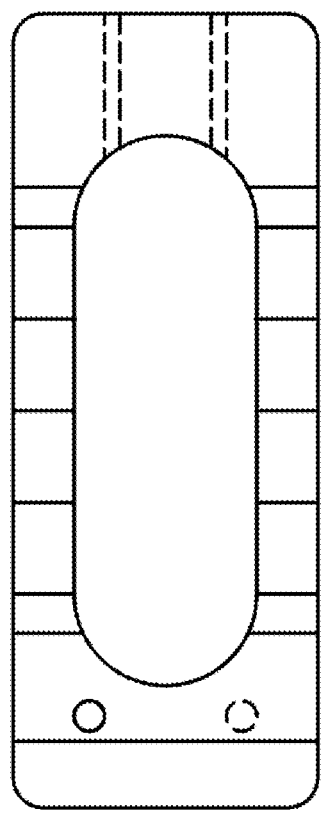
FIG. 1 is a schematic view of a conventional fusion cage.
Figure 2:
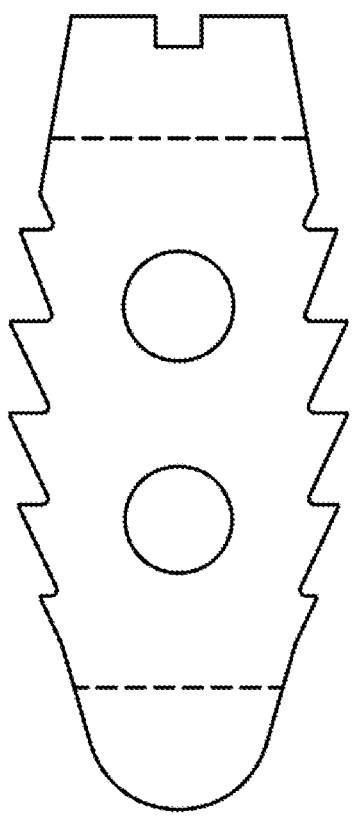
FIG. 2 is a top view of the conventional fusion cage.
Figure 3:
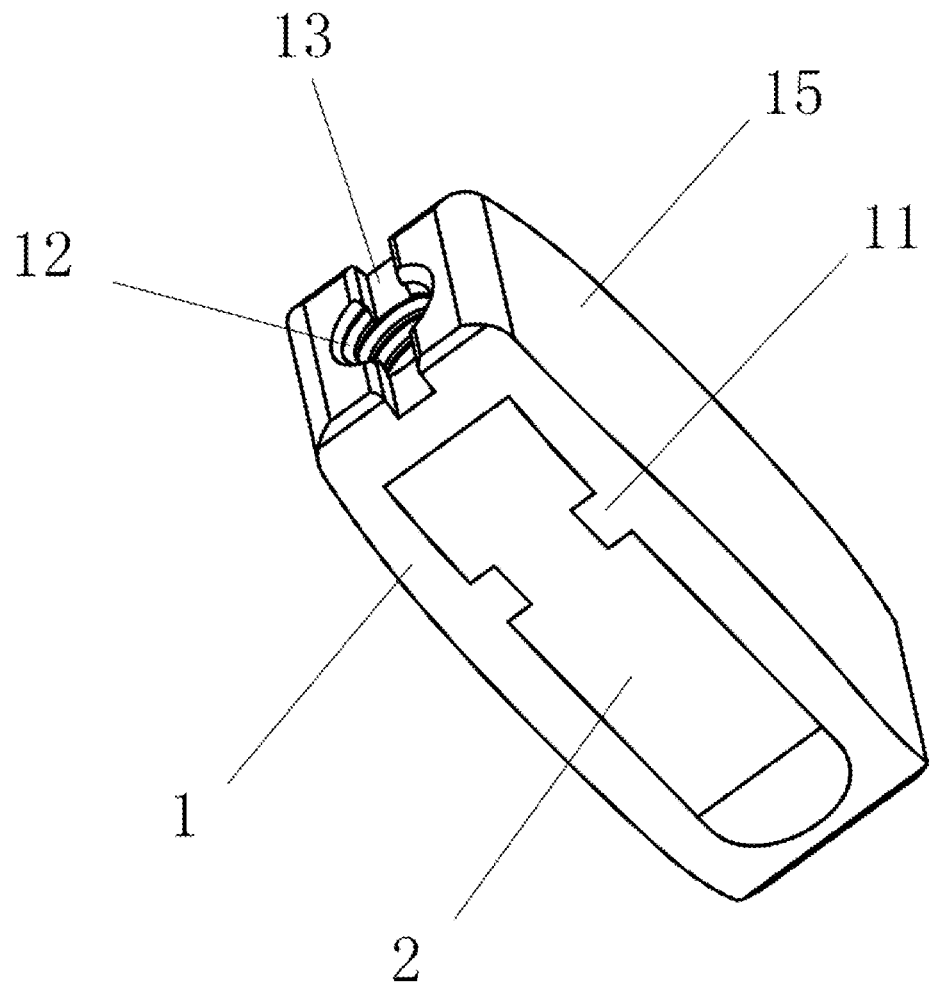
FIG. 3 is a front elevational view of the bone trabecular fusion cage of the present disclosure.
Figure 4:
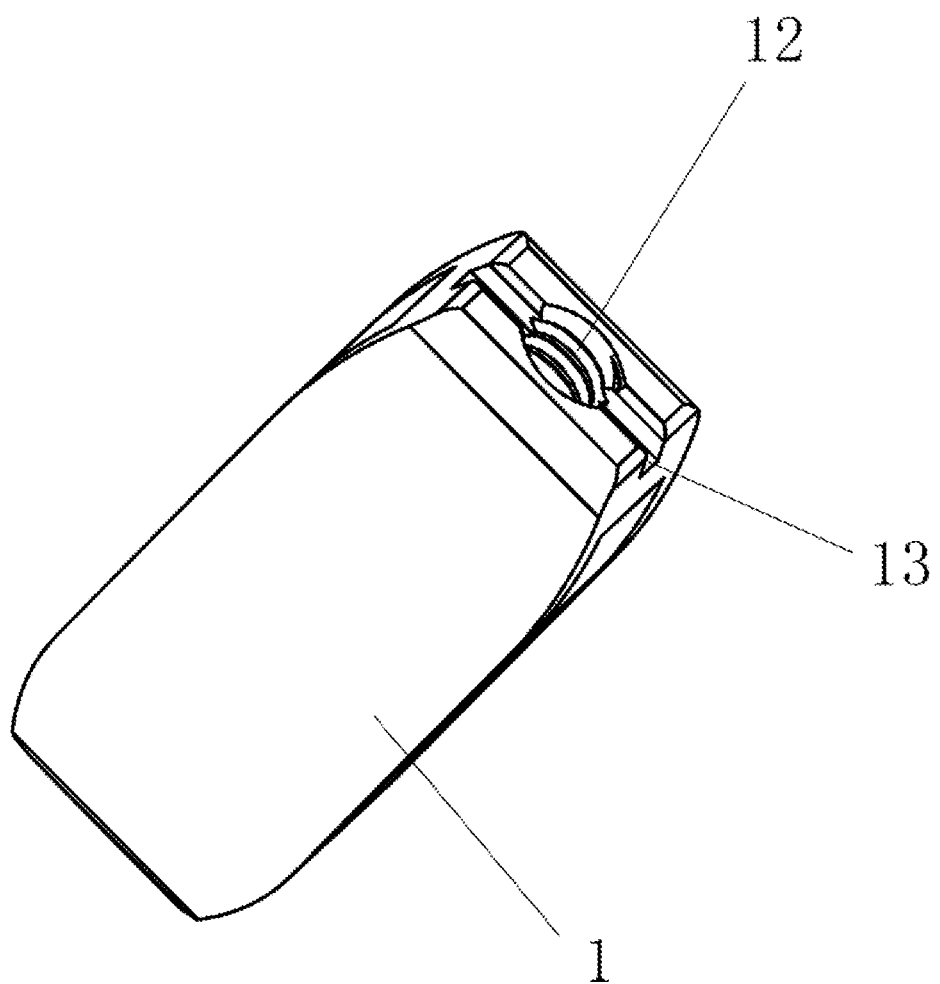
FIG. 4 is another elevational view of the bone trabecular fusion cage of the present disclosure.
Figure 5:
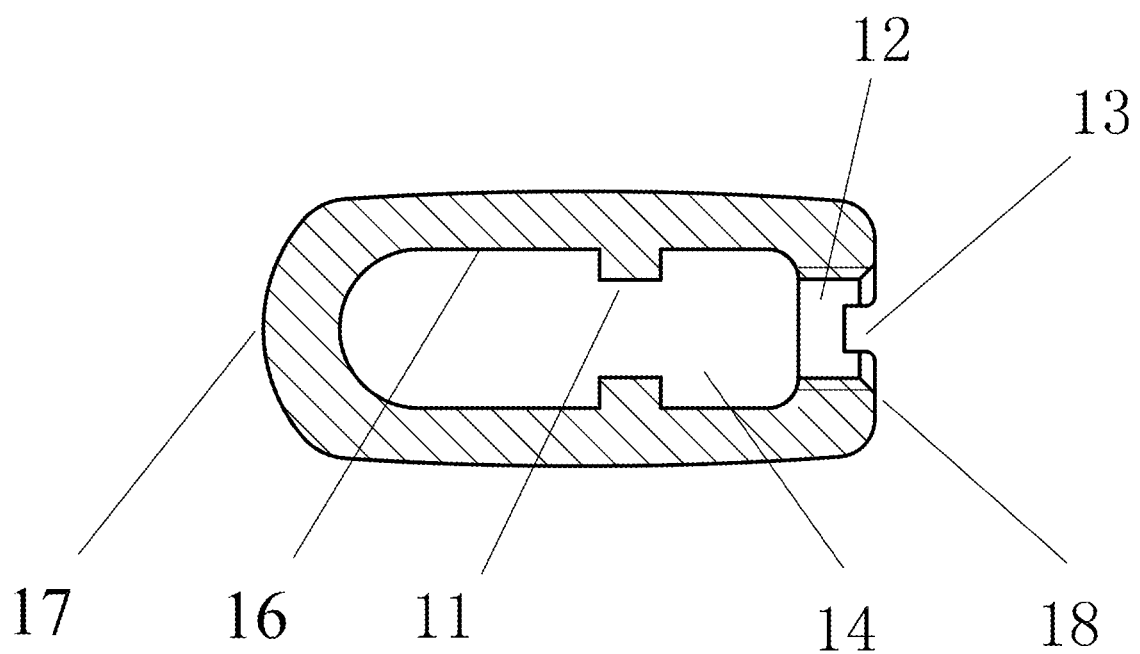
FIG. 5 is a schematic view of a bone trabecular housing of the bone trabecular fusion cage in the present disclosure.
Figure 6:
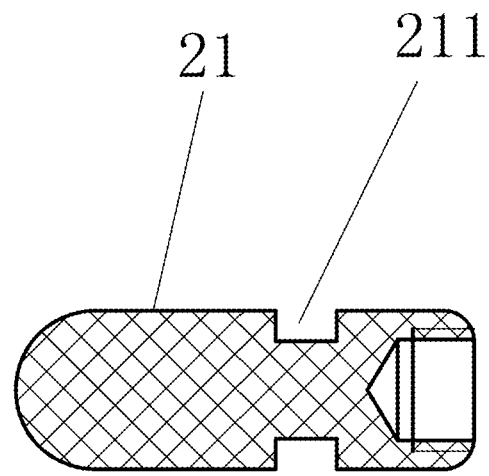
FIG. 6 is a schematic view of a liner of the bone trabecular fusion cage in the present disclosure.
Figure 7:
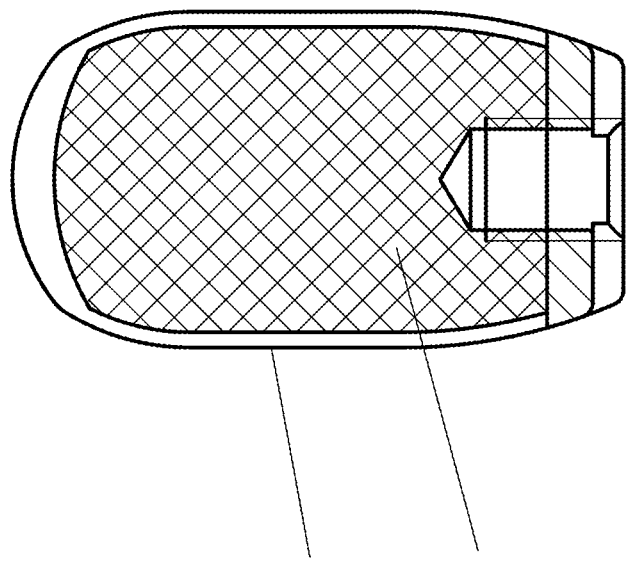
FIG. 7 is a schematic view of the pores on the side wall of the bone trabecular fusion cage.

FIG. 3 and FIG. 7 show a bone trabecular fusion cage of the present disclosure for implanting into an intervertebral disc, including a bone trabecular housing 1 and a liner 2. The bone trabecular housing 1 is made of titanium alloy powder material, and is sinter molded by metal 3D printing and electric fusion. The bone trabecular housing 1 is formed as a closed spaced enclosed by the left and right side wall 15, the flat end 18 and the upper and lower end 17, and has an open accommodation space 14 therein. A plurality of pores 151 are arranged on the side wall 15. The plurality of pores 151 form a hollow mesh structure on the side wall 15, and the sclerotin grows into the bone trabecular housing 1 through the pores 151, which is favorable for the bone to grow into the stable the bone trabecular fusion cage; in an alternative embodiment, the pores 151 do not pentrate the side wall 15, which enhances the stability of the bone trabecular fusion cage in the intervertebral disc. The liner 2 is made of polyether-ether-ketone (PEEK) material for reinforcing the strength of the liner 2. The liner is made by a four-axis machining center, and is fixed in the accommodation space 14 of the bone trabecular housing 1, which achieves good elastic modulus of bone. In this way, the bone fusion effect and the physiological activity of human body are enhanced. In the present disclosure, the combination of the bone trabecular housing 1 and the liner 2 of polyether-ether-ketone is implanted into the intervertebral disc. In the clinical operation, the hollow bone trabecular housing structure facilitates the implantation of the trabecular fusion cage prosthesis into the human body. Then, new bone can grow into the gaps of the bone trabecular housing structure, making the prosthesis more stable. Also, the polyether-ether-ketone (PEEK) liner is used to reinforce the strength of the bone trabecular fusion cage.

Further, an inner wall 16 of the bone trabecular housing 1 is provided with at least one protrusion 11, an outer wall 21 of the liner 2 is provided with a recess 211 matching with the protrusion 11, and the protrusion 11 of the bone trabecular housing 1 is embedded in the recess 211 of the liner 2 to securely connect the bone trabecular housing 1 and the liner 2. The protrusion 11 in the bone trabecular housing 1 is of beam-shape, and the recess 211 of the liner 2 has an interference fit with the beam-shaped protrusion 11 of the bone trabecular housing 1. The dimension tolerance of the protrusion 11 and the recess 211 can be sufficiently ensured by using a precise machine tool, so that the bone trabecular housing 1 and the liner 2 are well fitted.

Further, the bone trabecular housing 1 has a convex end 17 being arc-shaped at one end and a flat end 18 at the other end. An implantation hole 12 and implantation groove 13 for cooperating with the implantable surgical tool are provided on the flat end 18. The implantation hole 12 is a recess on an end face of the bone trabecular housing 1, and the implantation hole 12 is located in the implantation groove 14. The implantation hole 12 and the implantation groove 13 are coupled by an implantation surgical too, and the bone trabecular fusion cage is inserted into the intervertebral disc through the intervertebral space for fixation. From the doctor's point of view, the product can be operated conveniently and quickly during surgery. The surgery is accessed from one position, the wound is treated well, and good imaging effect of metal position is achieved, which greatly reduces the difficulty of surgery. Among them, the implantation hole 12 of the present disclosure is a threaded hole.

Further, an appearance of the bone trabecular housing 1 is a smooth transitional curvature, which gradually contracts from middle to opposite ends, the middle portion has a larger inner diameter than the end portions. The outer contour is curved according to the cross section of the patient's spine vertebral body, which is more suitable for the curvature of the patient's vertebral body. The specific shape is made according to the actual situation of the patient and conforms to the human anatomy, which enables the doctor to easily implant the implant into the human body.

According to the bone trabecular fusion cage of the present disclosure, The improved product does not require postoperative development after development of the needle, and the polyether-ether-ketone liner can provide good elastic modulus of bone. The bone trabecular housing can achieve better bone ingrowth. The product does not require bone grafting, and overcomes the problem that the singleness of the material makes the performance of the product greatly compromised. Also, better fusion effect and bone ingrowth effect are taken into consideration, the patient recovers quickly, and the fusion effect is good. By using the bone trabecular fusion cage, products implanted into patient bodies are safer and more effective. The shape and structure of the product are more in line with the human anatomy, which enables the doctor to easily implant the implant into the human body. Within a few months after implantation, the capillaries and related tissues will grow into the product along the pores of the housing, so that the implant is integrated with the human body and thus no loosening or displacement would occur. The product can be conveniently and easily implanted. Designed implantation instrument is used which is threadedly connected with the tail of the fusion cage, passes through the intervertebral space, and is implanted into the intervertebral disc pretreated with other instruments. The bone ingrowth after implantation is huge, which can stabilize the intervertebral disc, so that better bone fusion is achieved. Compared with other fusion cages that require bone grafting, the results will be much better. From the doctor's point of view, the product can be operated conveniently and quickly during surgery. The surgery is accessed from one position, the wound is treated well, and good imaging effect of metal position is achieved, which greatly reduces the difficulty of surgery.

The present disclosure has been described in detail with reference to the preferred embodiments thereof. However, it is noted that the detailed description of the present disclosure should not be construed as limitation to the essence and scope of the present disclosure. Various modifications to the embodiments made by those of ordinary skill in the art upon reading the description are intended to be within the protection scope of the present disclosure.

What is claimed is:

1. A bone trabecular fusion cage for implanting into an intervertebral disc, comprising:
    a bone trabecular housing (1) made of titanium alloy powder material with trabecular housing accommodation space therein, wherein two opposite side walls of the bone trabecular housing each form a hollow mesh structure by a plurality of pores of uniform size, the plurality of pores do not penetrate the two opposite side walls and are configured to allow sclerotin to grow into the bone trabecular housing (1) through the plurality of pores to securely fix the bone trabecular fusion cage in the intervertebral disc; and
    a liner (2) made of polyether-ether-ketone material, wherein the liner (2) is fixed in the trabecular housing accommodation space of the bone trabecular housing (1) and can be fused with the sclerotin grown into the plurality of pores of the bone trabecular housing;
    wherein at least one protrusion (11) is provided on an inner wall of the bone trabecular housing (1), an outer wall of the liner (2) is provided with at least one recess matching with the protrusion, and the protrusion of the bone trabecular housing (1) is embedded in the recess of the liner (2) to securely connect the bone trabecular housing (1) and the liner (2); an upper periphery of the liner (2) is blanketed by the bone trabecular housing (1), the protrusion (11) in the bone trabecular housing (1) is of beam-shape, and the recess of the liner (2) has an interference fit with the beam-shaped protrusion of the bone trabecular housing (1); an appearance of the bone trabecular housing is a smooth transitional curvature, which gradually tapers from middle to both ends; the curvature of an outer contour of the bone trabecular housing (1) configured to coincide with a cross-sectional curvature of a spinal vertebral body of a patient.

2. The bone trabecular fusion cage of claim 1, wherein an implantation hole (12) and an implantation groove (13) are disposed at one end of the bone trabecular housing, the implantation groove (13) is disposed on an end face of the bone trabecular housing (1), the implantation hole (12) is located in the implantation groove (13), wherein the bone trabecular fusion cage is configured to be inserted into the intervertebral disc through the intervertebral space for fixation by connection of an implantation surgical tool matching with the implantation hole (12) and the implantation groove (13) to the bone trabecular housing (1).

3. The bone trabecular fusion cage of claim 2, wherein the bone trabecular housing (1) has a convex end at one end and a flat end at the other end, and the implantation hole (12) and the implantation groove (13) are disposed on the flat end.

4. The bone trabecular fusion cage of claim 2, wherein the implantation hole (12) is a threaded hole.

5. The bone trabecular fusion cage of claim 1, wherein the plurality of pores on the side wall of the bone trabecular housing (1) form a hollow mesh structure.

* * * * *